(12) United States Patent
Kondo et al.

(10) Patent No.: US 7,629,479 B2
(45) Date of Patent: Dec. 8, 2009

(54) POLYGLYCEROL FATTY ACID ESTER AND COMPOSITION CONTAINING SAME

(75) Inventors: Naoki Kondo, Yokkaichi (JP); Kazuhito Uchida, Yokkaichi (JP); Yoshihiko Takase, Yokkaichi (JP); Takeshi Nakamura, Yokkaichi (JP); Toshio Endo, Otake (JP)

(73) Assignee: Taiyo Kagaku Co., Ltd., Yokkaichi-Shi (JP)

( * ) Notice: Subject to any disclaimer, the term of this patent is extended or adjusted under 35 U.S.C. 154(b) by 175 days.

(21) Appl. No.: 11/665,117

(22) PCT Filed: Oct. 6, 2005

(86) PCT No.: PCT/JP2005/018550

§ 371 (c)(1),
(2), (4) Date: Apr. 11, 2007

(87) PCT Pub. No.: WO2006/041011

PCT Pub. Date: Apr. 20, 2006

(65) Prior Publication Data

US 2009/0018358 A1      Jan. 15, 2009

(30) Foreign Application Priority Data

Oct. 12, 2004  (JP) .............................. 2004-298024
Jun. 13, 2005  (JP) .............................. 2005-172428

(51) Int. Cl.
*A23D 9/00*      (2006.01)

(52) U.S. Cl. ....................................... 554/227
(58) Field of Classification Search ................. None
See application file for complete search history.

(56) References Cited

U.S. PATENT DOCUMENTS

2002/0035238 A1      3/2002   Nakamura et al.

FOREIGN PATENT DOCUMENTS

| JP | 10-95749 | * | 1/1987 |
|---|---|---|---|
| JP | 62-419 | A | 1/1987 |
| JP | 06-192065 | A | 7/1994 |
| JP | 9-188754 | * | 7/1997 |
| JP | 9-188754 | A | 7/1997 |
| JP | 9-188755 | A | 7/1997 |
| JP | 10-95749 | * | 4/1998 |
| JP | 10-95749 | A | 4/1998 |
| JP | 2000-239208 | A | 9/2000 |
| JP | 2001-333703 | * | 12/2001 |
| JP | 2001-333703 | A | 12/2001 |
| JP | 2003-284510 | * | 10/2003 |
| JP | 2003-284510 | A | 10/2003 |
| JP | 2006-346526 | A | 12/2006 |

* cited by examiner

*Primary Examiner*—Deborah D Carr
(74) *Attorney, Agent, or Firm*—Birch, Stewart, Kolasch & Birch, LLP

(57) ABSTRACT

A polyglycerol fatty acid ester formed by esterifying a polyglycerol and a fatty acid, wherein the polyglycerol has a hydroxyl value of 1200 or less and primary hydroxyl groups in an amount of 50% or more of the total hydroxyl groups, and an emulsified or solubilized composition, foodstuff, and cosmetics, each containing the polyglycerol fatty acid ester.

12 Claims, No Drawings

POLYGLYCEROL FATTY ACID ESTER AND COMPOSITION CONTAINING SAME

TECHNICAL FIELD

The present invention relates to a polyglycerol fatty acid ester, which can be utilized as a surfactant for foods, cosmetics, pharmaceuticals, and industrial uses for the purpose of emulsification, solubilization, or the like, and a composition containing the polyglycerol fatty acid ester.

BACKGROUND ART

Conventional emulsifying agents or solubilizing agents are various compounds, for example, ethylene oxide-based nonionic surfactants such as polyoxyethylene alkyl ethers, polyoxyethylene polyhydric alcohol fatty acid esters, and polyoxyethylene alkylphenyl ethers, and ionic surfactants. In the field of foods, surfactants which are highly safe, such as sorbitan fatty acid esters, sucrose fatty acid esters, polyglycerol fatty acid esters, and polyglycerol condensed ricinoleates have been known. Among them, the polyglycerol fatty acid esters are the most useful surfactant because the polyglycerol fatty acid esters have high safety to human body and environment and the polyglycerol fatty acid esters can be obtained in various kinds of compositions, thereby giving high versatility.

Regarding the polyglycerol fatty acid esters, a polyglycerol fatty acid ester in which degree of polymerization and HLB of the polyglycerol are defined has been conventionally reported (see Patent Publication 1). However, a polyglycerol fatty acid ester in which a ratio of primary hydroxyl groups is defined has not been reported.

On the other hand, a polyglycerol used as a raw material for a polyglycerol fatty acid ester can be generally obtained by subjecting a glycerol used as a raw material to dehydration-condensation in the presence of a catalyst such as sodium hydroxide while heating, and purifying the reaction mixture by distillation, decolorization, deodorization, ion-exchange resin treatment, or the like, as occasion demands. The end point of the dehydration-condensation is usually determined by the measurement results of its hydroxyl value.

Patent Publication 1: Japanese Patent Laid-Open No. Hei 6-192065

DISCLOSURE OF INVENTION

Problems to be Solved by the Invention

A polyglycerol prepared by the steps as described above is a mixture of dehydration-condensation compounds of glycerol with different structures. The causations therefor include the fact that a molecular structure of the polyglycerol generated would vary depending on which of hydroxyl groups is involved in the reaction where the glycerol molecules themselves are condensed, because glycerol has two primary hydroxyl groups and one secondary hydroxyl group. The structure of the polyglycerol greatly affects the properties of a polyglycerol fatty acid ester. A presently commercially available polyglycerol fatty acid ester has not sufficiently exhibited its properties because the commercially available product has not been designed in consideration of the structure of a hydrophilic group in accordance with its purposes of use. The information reflecting a molecular structure of this polyglycerol can be obtained by various methods. However, a precise determination of the molecular structure would be insignificant because the commercially available product is composed of a mixture as mentioned above. However, molecular species having given tendencies can be increased by combining synthetic methods or purification methods even when the polyglycerol is in the form of a mixture. For example, a ratio of primary hydroxyl groups or secondary hydroxyl groups is one of these, and the ratio can be easily confirmed by determining a nuclear magnetic resonance spectrum as described later.

At present, a polyglycerol distributed in the market has a ratio of primary hydroxyl groups of less than 50%, so that an ester of the polyglycerol and a fatty acid has not been able to exhibit high emulsification and solubilization properties. For example, when a useful substance such as a fat-soluble vitamin such as vitamin E, or β-carotene is produced in the form of beverage using an existing surfactant for foods, or a surfactant for cosmetics and pharmaceuticals, such as a polyoxyethylene sorbitan ester, a beverage could not be solubilized transparently so that a manufactured article having excellent storage stability could not be produced. Therefore, an aid such as ethanol is necessitated to be added to obtain sufficient solubilization property. Accordingly, when an individual drinks the resulting beverage in a large quantity, the individual is in a state of ebriety, which has become a social problem especially among young people. Moreover, while a polyoxyethylene derivative has been used as a hydrophilic emulsifying agent in the cosmetics industry, there has been a disadvantage in safety such as skin irritation, so that a substitute product has been desired. However, conventional polyglycerol fatty acid esters or sucrose fatty acid esters cannot substitute therefor because their properties of emulsification, solubilization, and emulsion stability are insufficient.

Therefore, an object of the present invention is to provide a polyglycerol fatty acid ester enabling the production of a solubilized product or a stable emulsified product which could not have been produced from a conventional surfactant, and a composition containing the polyglycerol fatty acid ester.

Means to Solve the Problems

As a result of intensive studies in view of the above matters, the present inventors have accomplished the present invention. Specifically, the present invention relates to:

[1] a polyglycerol fatty acid ester formed by esterifying a polyglycerol and a fatty acid, wherein the polyglycerol has a hydroxyl value of 1200 or less and primary hydroxyl groups in an amount of 50% or more of the total hydroxyl groups;

[2] an emulsified or solubilized composition containing the polyglycerol fatty acid ester as defined in the above [1];

[3] foodstuff containing the polyglycerol fatty acid ester as defined in the above [1]; and

[4] cosmetics containing the polyglycerol fatty acid ester as defined in the above [1].

Effects of the Invention

According to the present invention, the production of a solubilized product or a stable emulsified product which could not have been produced from a conventional surfactant is enabled.

BEST MODE FOR CARRYING OUT THE INVENTION

The present invention will be explained in detail hereinbelow.

One of the great features of the polyglycerol fatty acid ester of the present invention resides in that the polyglycerol fatty acid ester is formed by esterifying a polyglycerol and a fatty acid, wherein the polyglycerol has a hydroxyl value of 1200 or less and primary hydroxyl groups in an amount of 50% or more of the total hydroxyl groups.

By having the above features, the polyglycerol fatty acid ester of the present invention can be used as a surfactant having excellent solubilization property and emulsification property.

The term "surfactant" in the present invention refers to a substance added for the purpose of stabilization upon mixing an oleophilic substance and a hydrophilic substance, the substance having strong surfactant property. These substances have both an oleophilic functional group and a hydrophilic functional group within the molecule, thereby lowering a surface tension of water.

The term "polyglycerol" in the present invention refers to a substance having a hydroxyl group and an ether bond within the molecule, wherein the substance is obtainable by subjecting glycerol to dehydration-condensation or the like.

The polyglycerol usable in the present invention is a polyglycerol, wherein the polyglycerol has primary hydroxyl groups in an amount of 50% or more of the total hydroxyl groups in the polyglycerol. The polyglycerol has primary hydroxyl groups in an amount of preferably 55% or more, and more preferably 60% or more, from the viewpoint of further improving solubilization property and emulsion stability of the resulting polyglycerol fatty acid ester. Further, the upper limit is not particularly defined, but it is desired that the amount is 90% or less in order to fully exhibit the effects. A ratio of primary hydroxyl groups occupied in the total hydroxyl groups in the polyglycerol of the present application would vary depending on a degree of condensation of the polyglycerol. Therefore, considering that kinds of a degree of polymerization of generally distributed polyglycerols are tetra, penta, hexa, and deca, upper limits thereof can be exemplified numerically as 70% or less and preferably 65% or less for tetraglycerol, 75% or less and preferably 70% or less for pentaglycerol, 80% or less and preferably 75% or less for hexaglycerol, and 85% or less and preferably 80% or less for decaglycerol. Further, a polyglycerol has a hydroxyl value of 1200 or less, and one having a hydroxyl value of 1100 or less is more preferable, and one having a hydroxyl value of 1000 or less is even more preferable, from the viewpoint of being capable of adjusting hydrophilicity (HLB) of a polyglycerol fatty acid ester in accordance with its applications. In addition, the polyglycerol having a hydroxyl value of 770 or more is preferable, from the viewpoint of operability and easiness in esterifying with a fatty acid.

The ratio of primary hydroxyl groups to the total hydroxyl groups can be determined by a method for determining a nuclear magnetic resonance spectrum (NMR) with respect to carbon atoms. In addition, the hydroxyl value can be determined by a method known in the art.

Here, a nuclear magnetic resonance spectrum with respect to carbon atoms can be determined as follows. Five-hundred milligrams of a polyglycerol is dissolved in 2.8 ml of heavy water, and the solution is filtrated. Thereafter, $^{13}$C-NMR (125 MHz) spectrum is obtained by gated decoupling. A peak intensity is proportional to the number of carbon atoms measured by gated decoupling technique. The $^{13}$C chemical shifts showing the presence of primary hydroxyl groups and secondary hydroxyl groups appears near 63 ppm for a methylene carbon ($CH_2OH$) and near 71 ppm for a methyne carbon (CHOH), respectively. Abundance ratios of primary hydroxyl groups and secondary hydroxyl groups are calculated by the analysis of signal intensities of each of two kinds. However, the methyne carbon (CHOH) showing a secondary hydroxyl group overlaps with a peak of a methylene carbon further adjoining a methyne carbon bound to the methylene carbon showing a primary hydroxyl group, so that an integration value of the methyne carbon itself cannot be obtained. Therefore, the integration value is calculated by a signal intensity near 74 ppm of a methylene carbon ($CH_2$) adjoining the methyne carbon (CHOH).

A general polyglycerol can be obtained by the steps of firstly heating glycerol under a normal pressure or a reduced pressure in the presence of an alkali catalyst, allowing a gas such as nitrogen or steam to pass therethrough, thereby removing a low-boiling component, or the like, and removing an ionic component such as a catalyst used with an ion-exchange resin, an ion-exchange membrane, or the like, removing a color component or an odor component using an adsorbent such as activated carbon, subjecting the reaction mixture to a reduction treatment such as hydrogenation, or fractionating the reaction mixture by molecular distillation or rectification, or the like, thereby purifying the mixture, in accordance with its purposes of use.

Alternatively, when the polyglycerol is produced from glycerol as a raw material as mentioned above, an undesirable by-product such as a six-membered ring or an eight-membered ring is generated in a large amount due to an intermolecular condensation upon dehydration-condensation. Therefore, a polyglycerol which hardly contains any by-products can be also prepared by synthesizing from glycidol, epichlorihydrin, or monochlorohydrin as a raw material so as not to generate these by-products, and purifying the reaction product.

Alternatively, when reacting a polyglycerol and a fatty acid, a reactivity with a fatty acid of a low-molecular-weight polyglycerol is generally higher than that of a high-molecular-weight polyglycerol, so that homogeneous esters cannot be produced when a polyglycerol having a wide molecular weight distribution is used as a raw material. Therefore, a polyglycerol having a molecular weight distribution as narrow as possible can be prepared, for example, by a dehalogenated alkali metal salt reaction using glycerol or a partial alcholate of a polymer of the glycerol and a halogenated hydrocarbon or an oxyhalogenated hydrocarbon as raw materials.

Alternatively, a commercially available polyglycerol such as Great Oil DE-1, Great Oil DE-2, or Great Oil TR-1, each manufactured by Taiyo Kagaku Co., Ltd., may be used as the polyglycerol.

The method of preparing a polyglycerol having primary hydroxyl groups in an amount of 50% or more of the total hydroxyl groups, usable in the present invention is not particularly limited. The polyglycerol can be obtained by, for example, fractionating and purifying a commercially available polyglycerol.

A reagent which is selectively subjected to a coupling reaction to a primary hydroxyl group, i.e., a reagent which serves as a protecting group of the primary hydroxyl group, is reacted to the polyglycerol prepared as described above, or a commercially available polyglycerol. In that case, the larger the number of primary hydroxyl groups in one molecule of a polyglycerol, the larger the number of protecting groups, so that a polarity of the polyglycerol is lowered consequently. On the other hand, a protecting group is less likely to be introduced into a polyglycerol containing a large amount of secondary hydroxyl groups, so that the polyglycerol still maintains its original high polarity. Both polyglycerols can be separated by utilizing this difference in polarity. A polyglycerol containing a large amount of primary hydroxyl groups can be obtained by subjecting the separated polyglycerol to an elimination treatment of the protecting group.

The reagent selectively reacting to a primary hydroxyl group usable in the present invention includes, for example, chlorotriphenylmethyl, isobutene, 1-tritylpyridinium tetrafluoroborate, and the like. As a polyglycerol without having a secondary hydroxyl group in addition to 1,2-diol, a compound for forming an acetonide with a polyglycerol (for example, methyl isopropenyl ether, 2,2-dimethoxypropane, 2,2-diethoxypropane, acetone, or the like) can also be used. Among them, chlorotriphenylmethane is preferable from the aspect of easiness of introducing and eliminating a primary hydroxyl group.

A reaction ratio of the polyglycerol and the reagent is properly adjusted depending on the number of primary hydroxyl groups in the desired polyglycerol. It is preferable that the reagent is used in excess to surely progress the reaction. For example, the reagent is used in an amount of preferably from 2 to 10 mol, and more preferably from 3 to 7 mol, based on 1 mol of the polyglycerol.

It is preferable that the reaction of the polyglycerol and the reagent is carried out in an organic solvent to improve reactivity. The organic solvent includes pyridine, dimethylformamide, and the like. The amount of the organic solvent is preferably from 200 to 1,000 parts by weight, and more preferably from 300 to 500 parts by weight, based on 100 parts by weight of the polyglycerol. Here, when a compound for forming an acetonide with a polyglycerol is used as a reagent, the same effects as those of adding a solvent can be expected by using the compound in a far excess amount.

The reaction of the polyglycerol and the agent is carried out at preferably from 5° to 30° C., and more preferably from 10° to 25° C., from the viewpoint of sureness in the progress of the reaction and in the protection.

After the termination of the reaction, a posttreatment may be carried out in the same manner as in an ordinary chemical reaction. The organic solvent such as pyridine can be removed by vacuum distillation.

A method of separating the polyglycerol of interest from the resulting reaction mixture can be achieved by utilizing chemical and physical differences of the polyglycerols into which protecting groups are introduced. For example, the polyglycerol of interest can be separated by a method such as distillation, vacuum distillation, or molecular distillation utilizing the difference in boiling points, or alternatively, the polyglycerol of interest can be fractionated by utilizing the difference in solubility to water or an organic solvent. For example, the polyglycerol of interest can be fractionated by dispersing the reaction mixture in water, and extracting the dispersion with a water-immiscible organic solvent (for example, chloroform, dichloromethane, petroleum ether, hexane, benzene, toluene, ether, ethyl acetate, or the like). When this fractionation method is used, a water-containing ethanol, or an inorganic salt solution such as brine or a sodium sulfate solution can also be used in place of water. It is preferable that the polyglycerol of interest is fractionated with water and ethyl acetate.

The solvents after extraction with the solvents are removed, whereby a polyglycerol derivative having low polarity, i.e., a polyglycerol in which a large number of protecting groups are introduced into one molecule is obtained. The elimination of a protecting group from this derivative can be carried out by an ordinary method according to organic synthesis. For example, the elimination of a protecting group can be achieved by a method of treatment with p-toluenesulfonic acid in methanol, a method including the step of heating the derivative in an aqueous acetic acid solution while stirring, or the like. As one example, when a triphenylmethyl group is introduced into a polyglycerol, a protecting group can be eliminated by the steps of adding an aqueous acetic acid solution to the resulting reaction mixture in an amount 2 to 3 times that of the mixture, and stirring the mixture at from 55° to 60° C. for 10 hours.

In addition, the polyglycerol usable in the present invention may be prepared by preparing a unit structure compound in which a ratio of primary hydroxyl groups is very high, and mixing the unit structure compound with a polyglycerol in which a ratio of primary hydroxyl groups is low. It is easy to prepare the polyglycerol if mixing is carried out in a hot-water bath. As a polyglycerol in which a ratio of primary hydroxyl groups is low, a commercially available polyglycerol is useful. If a ratio of primary hydroxyl groups is determined beforehand by a method for determining a nuclear magnetic resonance spectrum (NMR), a composition of interest can be easily obtained.

The polyglycerol having primary hydroxyl groups in an amount of 50% or more of the total hydroxyl groups, usable in the present invention can be obtained by the above-mentioned method, without intending to particularly limit to this method.

The preparation of a polyglycerol having a hydroxyl value of 1200 or less can be carried out by adjusting the steps for a polyglycerol reaction, for example, as follows. For example, when a polyglycerol is prepared by using a glycerol polymerization method, a hydroxyl value is lowered with the passage of the polymerization reaction time. Therefore, a polyglycerol having a hydroxyl value of 1200 or less can be easily obtained by confirming the step of lowering a hydroxyl value of the polyglycerol during the reaction.

The fatty acid usable in the present invention is not particularly limited, as long as the fatty acid is a substance which contains a carboxylic acid as a functional group, obtained by hydrolyzing a fat or oil extracted from a natural animal or plant, and purifying the reaction product with or without separation. Alternatively, a fatty acid obtained by chemically synthesizing petroleum or the like as a raw material may be used. Or alternatively, a fatty acid may be a substance obtained by reducing these fatty acids by hydrogenation or the like, a condensed fatty acid obtainable by polycondensation of a fatty acid containing a hydroxyl group, or a polymerized fatty acid obtainable by heat-polymerization of a fatty acid containing an unsaturated bond. In selecting these fatty acids, the fatty acids may be properly determined by taking a desired effect into consideration. Specific examples of the fatty acid usable in the present invention include behenic acid, stearic acid, lauric acid, myristic acid, oleic acid, isostearic acid, palmitic acid, capric acid, caprylic acid, caproic acid, condensed ricinoleic acid, condensed 12-hydroxystearic acid, erucic acid, palmitoleic acid, linoleic acid, linolenic acid, octylic acid, octanoic acid, ricinoleic acid, 12-hydroxystearic acid, and the like. Among them, lauric acid, stearic acid, isostearic acid, palmitic acid, myristic acid, oleic acid, and condensed ricinoleic acid are preferable from the viewpoint of emulsification and solubilization.

The esterification of the polyglycerol and the fatty acid is carried out in accordance with a known method in the art. For example, the esterification can be carried out under a normal pressure or a reduced pressure in the presence of an alkali catalyst, in the presence of an acidic catalyst, or in the absence of a catalyst. In addition, polyglycerol fatty acid esters having a variety of properties can be prepared by varying amounts of the polyglycerol and the fatty acid to be mixed. For example, when a polyglycerol fatty acid ester for use in a hydrophilic surfactant is obtained, a polyglycerol and a fatty acid may be formulated by calculating weights so as to be in equimolar amounts based on the calculations of a hydroxyl value of the polyglycerol and a molecular weight of the fatty acid. When a polyglycerol fatty acid ester for use in an oleophilic surfactant is obtained, the number of moles of the fatty acid may be increased. The resulting polyglycerol fatty acid ester may be further purified depending on a demand upon use of the manufactured article to be used. The purification method may be any known method and is not particularly limited. For example, the purification may be carried out by subjecting to a reaction product an adsorption treatment with activated carbon, activated clay, or the like, or a deodorization treatment under a reduced pressure with steam, nitrogen, or the like as a carrier gas, or alternatively washing a reaction product with an acid or an alkali, or subjecting a reaction product to molecular distillation.

Further, the polyglycerol fatty acid ester of the present invention may be used alone, or can be utilized as a composition in which other substance is added or mixed therewith in accordance with its purposes.

For example, in order to facilitate the handling of a polyglycerol fatty acid ester, other component can also be added. For example, ethanol, propylene glycol, glycerol, a polyglycerol, water, liquid sugar, a fat or oil, or the like may be added thereto in order to lower its viscosity. Alternatively, a powder prepared by adding a polysaccharide such as lactose or dextrin, or a protein such as caseinate to the polyglycerol fatty acid ester of the present invention may be used.

The polyglycerol fatty acid ester of the present invention may be also used as an emulsifying agent composition prepared by mixing the polyglycerol fatty acid ester with other surfactant, from the viewpoint of improving emulsion stability. The surfactant to be mixed includes nonionic surfactants such as glycerol fatty acid esters, propylene glycol fatty acid esters, sucrose fatty acid esters, and polyglycerol fatty acid esters (with proviso that the polyglycerol fatty acid ester of the present invention is excluded); amphoteric surfactants; anionic surfactants; cationic surfactants; natural product-derived surfactants such as lecithin, zymolytic lecithin, or saponin; or the like.

Further, an oily substance may be mixed with the polyglycerol fatty acid ester of the present invention, to provide an emulsified or solubilized composition. The oily substance in this case is not particularly limited, and can be exemplified by, for example, a fat-soluble vitamin such as vitamin A, vitamin D, vitamin E, or vitamin K; an oil-soluble pigment such as carotene, carotenoid-based pigment, annatto pigment, or turmeric pigment; a natural flavor such as orange oil, lemon oil, ambrette seed oil, orrisroot oil, cananga oil, caraway oil, carrot seed oil, grapefruit oil, ginger oil, hop oil, milton oil, rose oil, or rosemary oil; a synthetic flavor such as eugenol, ethyl caprylate, geraniol, menthol, citral, citronnelle, or borneol; a spice extract such as curcuma extract, sesame extract, capsicum extract, garlic extract, or Japanese horseradish extract; a hydrophobic antioxidant such as oryzanol, rice bran oil extract, or tocopherol; a fatty acid such as oleic acid, linoleic acid, linolenic acid, arachidonic acid, eicosapentaenoic acid, docosapentaenoic acid, or prostaglandin; or a fatty acid derivative such as an ester thereof, a fat or oil such as olive oil, corn oil, safflower oil, fish oil, shark liver oil, or rice bran oil; or a physiologically active component or a useful component such as beeswax, rice wax, propolis, or octacosanol. In addition, in case where the oily substance is exemplified remarking on a chemical structure from another viewpoint, the oily substance includes terpenoids such as monoterpene, sesquiterpene, diterpene, and triterpene; carotenoids; steroids; phenyl propanoids; quinones such as benzoquinone, naphthoquinone, and anthraquinone; γ-pyrones; flavonoids such as flavone, flavonol, flavanone, dihydroflavonol, isoflavone, chalcone, aurone, anthocyanin, and neoflavanoid; α-pyrones such as monocyclic α-pyrones, coumarins, isocoumarins, and phthalides; aromatic compounds such as diarylheptanoids, stilbene, phloroglucin, and naphthalene; and nitrogen-containing compounds and sulfur-containing compounds such as pyrrole derivatives, pyrazole derivatives, imidazole derivatives, isoxazole derivatives, thiazole derivatives, pyridine derivatives, pyrimidine derivatives, pyrazine derivatives, indole derivatives, hydantoin derivatives, purine derivatives, pteridine derivatives, porphyrin derivatives, and capsaicins. These oily substances may be used alone, or in admixture of two or more kinds of the oily substances in accordance with its purposes.

In the preparation of the emulsified or solubilized composition of this oily substance, in addition to the polyglycerol fatty acid ester of the present invention and the oil-soluble substance, a polyhydric alcohol is recommended to be blended for the purpose of improving stability of the composition or improving stability upon dispersion of the composition in water. The polyhydric alcohol in this case is not particularly limited, and can be exemplified by glycerol, propylene glycol, polyglycerol, or liquid sugar, and glycerol can be preferably utilized especially from the aspect of safety and easy handling. In addition, other emulsifying agent or a solvent such as water or ethanol can be supplementally used. A blending ratio of the polyglycerol fatty acid ester of the present invention, the oily substance, and the polyhydric alcohol is not particularly limited, and these substances may be blended in any ratio in accordance with physical properties of the only substance or its purposes of use. If a recommended blending ratio is exemplified from the aspect of stability of the emulsified or solubilized composition, easy handling, stability during the dispersion in water, recommended blending ratios can be listed as follows: 1 to 40 parts by weight, and preferably from 5 to 20 parts by weight of the polyglycerol fatty acid ester of the present invention; 2 to 50 parts by weight, and preferably from 2 to 30 parts by weight of the oily substance; and 20 to 90 parts by weight, and preferably from 50 to 80 parts by weight of the polyhydric alcohol.

The method of use of the polyglycerol fatty acid ester composition of the present invention is not particularly limited, and the composition can be utilized in foodstuff, cosmetics, pharmaceuticals and industrial purposes for the purposes of emulsification, solubilization, dispersion, washing, foaming, defoaming, permeation, antibacterial action, and the like, and especially when utilized in foodstuff, in addition to those applications, the composition can be used in the modifications of starches, proteins and fats and oils. The composition is specifically applied as follows. In the field of foodstuff, the composition can be applied to instant foods such as instant noodles, retort pouch foods, canned foods, microwave-cooking foods, instant soups and miso soups, and freeze-dried foods; beverages such as soft drinks, fruits juice beverages, vegetable-based beverages, soya milk beverages, coffee beverages, tea beverages, powdered drinks, concentrate beverages, nutritious beverages, and alcoholic beverages; flour products such as bread, pastas, noodles, cake mix, deep frying powder, and bread crumbs; confectioneries such as caramel, candies, chewing gums, chocolate, cookies, biscuits, cakes, pies, snacks, crackers, Japanese sweets, and desert confectioneries; seasonings such as sauces, tomato-based seasonings, flavor seasonings, culinary mix, gravy sauces, dressings, clear soups, and roux for curry sauce and stew; fats and oils such as processed fats and oils, butter, margarine, and mayonnaise; milk products such as milk beverages, yogurts, lactobacilli beverages, ice creams, and creams; marine processed products such as frozen foods, hams and sausages made of fish, and marine pastes; livestock processed products such as livestock ham and sausages; agricultural processed products such as agricultural canned foods, jams and marmalades, pickles, cooked beans, and cereals; nutritional foods; and the like. In addition, in the field of the cosmetics, the composition can be applied to cleaning agents such as soaps, cleansing lotions, shampoos, and rinses; skin-care products such as skin lotions, milky lotions, skin creams, facial packs, hair tonics, and hair creams; finishing cosmetics such as lipsticks, eye shadows, hair setting lotions, and hairdressings; fragrances such as perfumes and lotions; oral use cosmetics such as dentifrice and mouthwash; and the like. In the field of industry, the composition can be applied to dispersion of a filler, a pigment, or a paint in a resin, and a tarnish prevention. In the field of food industry, the composition can be used as cleaning agents for equipments, processing aids, detergents for vegetables and fruits; and the like. The applications of the composition are not limited to those listed above.

EXAMPLES

The present invention will be further specifically explained hereinbelow by means of Examples, without intending to limit the present invention thereto.

Preparation Example 1

Purification of Polyglycerol

A three-necked flask equipped with a thermometer, Dimroth, and a stirrer was charged with 200 g of a polyglycerol manufactured by Taiyo Kagaku Co., Ltd. (Great Oil DE-1, decaglycerol; hydroxyl value: 890, ratio of primary hydroxyl groups: 46.6%, ratio of secondary hydroxyl groups: 53.4%) and 600 ml of pyridine. Thereto was added 370 g of chlorotriphenylmethyl (manufactured by Wako Pure Chemical Industries), a reagent selectively reacting with a primary hydroxyl group, and the mixture was stirred at 100° C. for 1 hour. Thereafter, the mixture was cooled to room temperature and stirred for 24 hours. Further, a majority of pyridine was removed from the reaction solution under a reduced pressure. Eight-hundred milliliters of water was added to the resulting reaction product, and the mixture was transferred to a separatory funnel and extracted with 400 ml of ethyl acetate 3 times. The ethyl acetate layers were combined, and concentrated, and a three-necked flask equipped with a thermometer, Dimroth, and a stirrer was charged with 156 g of the resulting residue and 300 g of acetic acid. The mixture was heated under reflux for 8 hours to eliminate a trimethylphenyl group. The above steps were repeated, and the purified polyglycerol was mixed, to give a certain amount of the polyglycerol. The resulting polyglycerol had a hydroxyl value of 866, a ratio of primary hydroxyl groups of 61.3%, and a ratio of secondary hydroxyl groups of 38.7%.

The hydroxyl value was calculated according to the Japan's Specifications and Standards for Food Additives, 7th Ed. "Fats and Related Substances Tests" or Standard Methods for the Analysis of Fats, Oils and Related Materials.

The ratios of primary hydroxyl groups and secondary hydroxyl groups were determined by spectrum analysis in a nuclear magnetic resonance apparatus. More specifically, ratios of primary hydroxyl groups and secondary hydroxyl groups of a polyglycerol fractionated as mentioned above were analyzed by using a nuclear magnetic resonance apparatus ($^{13}$C-NMR) (JNM-A500, manufactured by JEOL Ltd.). Five-hundred milligrams of the fractionated polyglycerol was dissolved in 2.8 ml of heavy water, and the solution was filtrated. Thereafter, $^{13}$C-NMR (125 MHz) spectrum was obtained by gated decoupling. A peak intensity is proportional to the number of carbon atoms measured by gated decoupling technique. The $^{13}$C chemical shifts showing the presence of primary hydroxyl groups and secondary hydroxyl groups appear near 63 ppm for a methylene carbon ($CH_2OH$) and near 71 ppm for a methyne carbon (CHOH), respectively. Abundance ratios of primary hydroxyl groups and secondary hydroxyl groups were calculated by the analysis of signal intensities of each of two kinds. Here, the methyne carbon (CHOH) showing a secondary hydroxyl group overlapped with a peak of a methylene carbon further adjoining a methyne carbon bound to the methylene carbon showing a primary hydroxyl group, so that an integration value of the methyne carbon itself could not be obtained. Therefore, the integration value was calculated by a signal intensity near 74 ppm of the methylene carbon ($CH_2$) adjoining the methyne carbon (CHOH).

Incidentally, hydroxyl values and ratios of primary hydroxyl groups and secondary hydroxyl groups in the following Preparation Examples 2 to 6 were also calculated in the same manner as above.

Preparation Example 2

Purification of Polyglycerol

A polyglycerol manufactured by Taiyo Kagaku Co., Ltd. (Great Oil DE-2, decaglycerol) was purified in the same manner as in Preparation Example 1. The resulting polyglycerol had a hydroxyl value of 883, a ratio of primary hydroxyl groups of 56.2%, and a ratio of secondary hydroxyl groups of 43.8%.

Preparation Example 3

Purification of Polyglycerol

A polyglycerol manufactured by Taiyo Kagaku Co., Ltd. (Great Oil TR-1, triglycerol; hydroxyl value: 1160, ratio of primary hydroxyl groups: 38.5%, ratio of secondary hydroxyl groups: 61.5%) was purified in the same manner as in Preparation Example 1. The resulting polyglycerol had a hydroxyl value of 1148, a ratio of primary hydroxyl groups of 52.5%, and a ratio of secondary hydroxyl groups of 47.5%.

Preparation Example 4

Purification of Polyglycerol

A three-necked flask equipped with a thermometer, Dimroth, and a stirrer was charged with 450 g of the residue obtained by concentrating an aqueous layer portion of Preparation Example 1 and 900 g of acetic acid. The mixture was heated under reflux for 8 hours to eliminate a trimethylphenyl group. The above steps were repeated, and the purified polyglycerol was mixed, to give a certain amount of the polyglycerol. The resulting polyglycerol had a hydroxyl value of 893, a ratio of primary hydroxyl groups of 34.4%, and a ratio of secondary hydroxyl groups of 65.6%.

Preparation Example 5

Purification of Polyglycerol

A three-necked flask equipped with a thermometer, Dimroth, and a stirrer was charged with 450 g of the residue obtained by concentrating an aqueous layer portion of Preparation Example 3 and 900 g of acetic acid. The mixture was heated under reflux for 8 hours to eliminate a trimethylphenyl group. The above steps were repeated, and the purified polyglycerol was mixed, to give a certain amount of the polyglycerol. The resulting polyglycerol had a hydroxyl value of 1165, a ratio of primary hydroxyl groups of 32.2%, and a ratio of secondary hydroxyl groups of 67.8%.

Preparation Example 6

Purification of Polyglycerol

A polyglycerol manufactured by Taiyo Kagaku Co., Ltd. (Great Oil DI-1, diglycerol; hydroxyl value: 1353, ratio of primary hydroxyl groups: 48.1%, ratio of secondary hydroxyl groups: 51.9%) was purified in the same manner as in Preparation Example 1. The resulting polyglycerol had a hydroxyl value of 1350, a ratio of primary hydroxyl groups of 53.5%, and a ratio of secondary hydroxyl groups of 46.5%.

Example A-1

A 300-mL four-necked flask was charged with 126 g of the polyglycerol purified in Preparation Example 1, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3. The acid value was calculated according to the Japan's Specifications and Standards for Food Additives, 7th Ed. "Fats and Related Substances Tests" or Standard Methods for the Analysis of Fats, Oils and Related Materials.

Acid values in the following Examples and Comparative Examples were also calculated in the same manner.

Example A-2

A 300-mL four-necked flask was charged with 135.2 g of the polyglycerol obtained in Preparation Example 1, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Example A-3

A 300-mL four-necked flask was charged with 126 g of the polyglycerol obtained in Preparation Example 2, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.2.

Example A-4

A 300-mL four-necked flask was charged with 135.2 g of the polyglycerol obtained in Preparation Example 2, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.4.

Example A-5

A 300-mL four-necked flask was charged with 126 g of the polyglycerol obtained in Preparation Example 3, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Example A-6

A 300-mL four-necked flask was charged with 135.2 g of the polyglycerol obtained in Preparation Example 3, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Example A-7

A 300-mL four-necked flask was charged with 130 g of the polyglycerol obtained in Preparation Example 3, 49.5 g of myristic acid and 0.06 g of sodium hydroxide, and the mixture was reacted at 240° C. under nitrogen gas stream while removing the generated water. After the reaction, 0.2 mL of phosphoric acid was added thereto to give polyglycerol myristate. This ester had an acid value of 0.5.

Example A-8

A 300-mL four-necked flask was charged with 126 g of the polyglycerol obtained in Preparation Example 3, 54 g of oleic acid and 0.06 g of sodium hydroxide, and the mixture was reacted at 240° C. under nitrogen gas stream while removing the generated water. After the reaction, 0.2 mL of phosphoric acid was added thereto to give polyglycerol oleate. This ester had an acid value of 0.4.

Comparative Example A-1

A 300-mL four-necked flask was charged with 126 g of the polyglycerol obtained in Preparation Example 4, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Comparative Example A-2

A 300-mL four-necked flask was charged with 135.2 g of the polyglycerol obtained in Preparation Example 4, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Comparative Example A-3

A 300-mL four-necked flask was charged with 126 g of a polyglycerol manufactured by Taiyo Kagaku Co., Ltd. (Great Oil DE-1, decaglycerol), 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Here, the polyglycerol manufactured by Taiyo Kagaku Co., Ltd. (Great Oil DE-1, decaglycerol) had a hydroxyl value of 890, a ratio of primary hydroxyl groups of 46.6%, and a ratio of secondary hydroxyl groups of 53.4%.

Comparative Example A-4

A 300-mL four-necked flask was charged with 135.2 g of a polyglycerol manufactured by Taiyo Kagaku Co., Ltd. (Great Oil DE-1, decaglycerol), 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Comparative Example A-5

A 300-mL four-necked flask was charged with 126 g of the polyglycerol obtained in Preparation Example 5, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Comparative Example A-6

A 300-mL four-necked flask was charged with 135.2 g of the polyglycerol obtained in Preparation Example 5, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Comparative Example A-7

A 300-mL four-necked flask was charged with 135 g of the polyglycerol obtained in Preparation Example 5, 49.5 g of myristic acid and 0.06 g of sodium hydroxide, and the mixture was reacted at 240° C. under nitrogen gas stream while removing the generated water. After the reaction, 0.2 mL of phosphoric acid was added thereto to give polyglycerol myristate. This ester had an acid value of 0.5.

Comparative Example A-8

A 300-mL four-necked flask was charged with 126 g of the polyglycerol obtained in Preparation Example 5, 45 g of oleic acid and 0.06 g of sodium hydroxide, and the mixture was reacted at 240° C. under nitrogen gas stream while removing the generated water. After the reaction, 0.2 mL of phosphoric acid was added thereto to give polyglycerol oleate. This ester had an acid value of 0.5.

Comparative Example A-9

A 300-mL four-necked flask was charged with 126 g of a polyglycerol manufactured by Taiyo Kagaku Co., Ltd. (Great Oil TR-1, triglycerol), 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Here, the polyglycerol manufactured by Taiyo Kagaku Co., Ltd. (Great Oil TR-1, triglycerol) had a hydroxyl value of 1160, a ratio of primary hydroxyl groups of 38.5%, and a ratio of secondary hydroxyl groups of 61.5%.

Comparative Example A-10

A 300-mL four-necked flask was charged with 135.2 g of a polyglycerol manufactured by Taiyo Kagaku Co., Ltd. (Great Oil TR-1, triglycerol), 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.5.

Comparative Example A-11

A 300-mL four-necked flask was charged with 126 g of the polyglycerol obtained in Preparation Example 6, 54 g of stearic acid and 0.06 g of sodium hydroxide, and the mixture was reacted at 250° C. under nitrogen gas stream while removing the generated water. After the reaction, 0.2 mL of phosphoric acid was added thereto to give polyglycerol stearate. This ester had an acid value of 0.3.

Comparative Example A-12

A 300-mL four-necked flask was charged with 135.2 g of the polyglycerol obtained in Preparation Example 6, 44.5 g of lauric acid and 0.06 g of sodium hydroxide, and the mixture was reacted at 240° C. under nitrogen gas stream while removing the generated water. After the reaction, 0.2 mL of phosphoric acid was added thereto to give polyglycerol laurate. This ester had an acid value of 0.4.

Test Example A-1

To 0.13 parts by weight of a commercially available 80% purity vitamin E was added 0.4 parts by weight of the polyglycerol fatty acid ester obtained in each of Examples A-1 to A-8 or Comparative Examples A-1 to A-12, and the mixture was heated to 80° C. and mixed for 10 minutes. To 100 mL of water warmed to 60° C. was added 0.063 g of the resulting mixture, and the mixture was stirred using a stirrer bar for 5 minutes. Turbidity of the mixture was determined in terms of absorbance at a wavelength 650 nm with a spectrophotometer (U-3210, manufactured by Hitachi, Ltd.). The results are shown in Table A-1.

It is clear from Table A-1 that the polyglycerol fatty acid esters in which a polyglycerol having a hydroxyl value of 1200 or less and a ratio of primary hydroxyl groups of 50% or more is used have excellent solubilization property.

Test Example A-2

One part by weight of the polyglycerol fatty acid ester obtained in each of Examples A-1 to A-8 or Comparative Examples A-1 to A-12 was dissolved in 100 parts by weight of water. While stirring the solution with a homomixer at 5,000 rpm, 100 parts by weight of soybean refined oil warmed to 60° C. was added to the solution, and thereafter the mixture was stirred at 10,000 rpm for 2 minutes, to give an O/W emulsion. The resulting emulsion was allowed to stand at 60° C. for 12 hours, and evaluated for O/W emulsion stability in accordance with the following evaluation criteria. The results are shown in Table A-1.

<O/W Emulsion Stability>

⊚: no difference from that immediately after preparation

○: oil layer being separated (less than about 5% of oil component)

Δ: oil layer being separated (about 5% to about 10% of oil component)

X: oil layer being separated (more than about 10% of oil component)

Here, ⊚ and ○ are defined as acceptable products.

TABLE 1

Table A-1

| | Polyglycerol | | | Physical Properties | |
|---|---|---|---|---|---|
| | Hydroxyl Value | Primary Hydroxyl Groups (%) | Fatty Acid | Transmittance (% 650 nm) | O/W Emulsion Stability |
| Ex. A-1 | 886 | 61.3 | Stearic Acid | 98.3 | ◎ |
| Ex. A-2 | 886 | 61.3 | Lauric Acid | 97.9 | ◎ |
| Ex. A-3 | 883 | 56.2 | Stearic Acid | 92.6 | ◎ |
| Ex. A-4 | 883 | 56.2 | Lauric Acid | 91.1 | ◎ |
| Ex. A-5 | 1148 | 52.5 | Stearic Acid | 88.6 | ◎ |
| Ex. A-6 | 1148 | 52.5 | Lauric Acid | 89.1 | ○ |
| Ex. A-7 | 1148 | 52.5 | Myristic Acid | 88.7 | ○ |
| Ex. A-8 | 1148 | 52.5 | Oleic Acid | 88.1 | ◎ |
| Comp. Ex. A-1 | 893 | 34.4 | Stearic Acid | 42.5 | X |
| Comp. Ex. A-2 | 893 | 34.4 | Lauric Acid | 48.2 | X |
| Comp. Ex. A-3 | 890 | 46.6 | Stearic Acid | 76.3 | Δ |
| Comp. Ex. A-4 | 890 | 46.6 | Lauric Acid | 72.1 | Δ |
| Comp. Ex. A-5 | 1165 | 32.2 | Stearic Acid | 40.6 | X |
| Comp. Ex. A-6 | 1165 | 32.2 | Lauric Acid | 39.2 | X |
| Comp. Ex. A-7 | 1165 | 32.2 | Myristic Acid | 40.3 | X |
| Comp. Ex. A-8 | 1165 | 32.2 | Oleic Acid | 38.4 | Δ |
| Comp. Ex. A-9 | 1160 | 38.5 | Stearic Acid | 55.3 | Δ |
| Comp. Ex. A-10 | 1160 | 38.5 | Lauric Acid | 53.2 | X |
| Comp. Ex. A-11 | 1350 | 53.5 | Stearic Acid | 50.3 | X |
| Comp. Ex. A-12 | 1350 | 53.5 | Lauric Acid | 47.7 | X |

It is clear from Table A-1 that the polyglycerol fatty acid esters in which a polyglycerol having a hydroxyl value of 1200 or less and a ratio of primary hydroxyl groups of 50% or more is used have excellent O/W emulsion stability.

Test Example A-3

Twenty parts by weight of glycerol was added to 10 parts by weight of the polyglycerol fatty acid ester obtained in each of Examples A-2, A-4 and A-6 and Comparative Examples A-2, A-4, A-6, A-10 and A-12, and the mixture was warmed to 50° C. While stirring with a glass rod, 80 parts by weight of silicone oil warmed to 50° C. was gradually added to the mixture, to give an emulsified composition. The resulting emulsified composition was allowed to stand and stored at 40° C. for 1 month, and evaluated for emulsion stability in accordance with the following evaluation criteria. The results are shown in Table A-2.

<Emulsion Stability>

◎: no difference from that immediately after preparation

○: white turbid

Δ: oil layer being separated (less than about 10% of oil component)

X: oil layer being separated (about 10% or more of oil component)

Here, ◎ and ○ are defined as acceptable products.

TABLE 2

Table A-2

| | Emulsion Stability |
|---|---|
| Ex. A-2 | ◎ |
| Ex. A-4 | ◎ |
| Ex. A-6 | ○ |
| Comp. Ex. A-2 | X |
| Comp. Ex. A-4 | Δ |
| Comp. Ex. A-6 | X |
| Comp. Ex. A-10 | X |
| Comp. Ex. A-12 | X |

It is clear from Table A-2 that the polyglycerol fatty acid esters in which a polyglycerol having a hydroxyl value of 1200 or less and a ratio of primary hydroxyl groups of 50% or more is used have excellent emulsion stability.

Test Example B-1

An emulsion dressing was prepared by using the polyglycerol fatty acid ester obtained in each of Examples A-1 to A-8 or Comparative Examples A-1 to A-12 in accordance with the composition shown in Table B-1. Acetic acid, table salt and an emulsifying agent were added to water, and the mixture was heated to 60° C. while stirring with a homomixer at 5,000 rpm, and corn oil separately heated to 60° C. was gradually added thereto. Thereafter, the mixture was emulsified at 10,000 rpm for 5 minutes. After the emulsion was stored at 40° C. for 5 days, emulsion stability was evaluated by visual examination.

TABLE 3

Table B-1

| | Blending Amount (% by weight) |
|---|---|
| Corn Oil | 65 |
| Acetic Acid | 15 |
| Table Salt | 2 |
| Water | 17 |
| Polyglycerol Fatty Acid Ester | 1 |

TABLE 4

Table B-2

| | Polyglycerol | | | |
|---|---|---|---|---|
| | Hydroxyl Value | Primary Hydroxyl Groups (%) | Fatty Acid | Emulsion Stability |
| Ex. A-1 | 886 | 61.3 | Stearic Acid | ◉ |
| Ex. A-2 | 886 | 61.3 | Lauric Acid | ◉ |
| Ex. A-3 | 883 | 56.2 | Stearic Acid | ○ |
| Ex. A-4 | 883 | 56.2 | Lauric Acid | ○ |
| Ex. A-5 | 1148 | 52.5 | Stearic Acid | ○ |
| Ex. A-6 | 1148 | 52.5 | Lauric Acid | ○ |
| Ex. A-7 | 1148 | 52.5 | Myristic Acid | ○ |
| Ex. A-8 | 1148 | 52.5 | Oleic Acid | ○ |
| Comp. Ex. A-1 | 893 | 34.4 | Stearic Acid | X |
| Comp. Ex. A-2 | 893 | 34.4 | Lauric Acid | X |
| Comp. Ex. A-3 | 890 | 46.6 | Stearic Acid | X |
| Comp. Ex. A-4 | 890 | 46.6 | Lauric Acid | Δ |
| Comp. Ex. A-5 | 1165 | 32.2 | Stearic Acid | Δ |
| Comp. Ex. A-6 | 1165 | 32.2 | Lauric Acid | X |
| Comp. Ex. A-7 | 1165 | 32.2 | Myristic Acid | X |
| Comp. Ex. A-8 | 1165 | 32.2 | Oleic Acid | Δ |
| Comp. Ex. A-9 | 1160 | 38.5 | Stearic Acid | Δ |
| Comp. Ex. A-10 | 1160 | 38.5 | Lauric Acid | X |
| Comp. Ex. A-11 | 1350 | 53.5 | Stearic Acid | Δ |
| Comp. Ex. A-12 | 1350 | 53.5 | Lauric Acid | X |

<Emulsion Stability>
◉: no difference from that immediately after preparation
○: oil layer being separated (less than about 5% of oil component)
Δ: oil layer being separated (about 5% to about 10% of oil component)
X: oil layer being separated (more than about 10% of oil component)
Here, ◉ and ○ are defined as acceptable products.

It is clear from Table B-2 that the emulsion dressings in which a polyglycerol having a hydroxyl value of 1200 or less and a ratio of primary hydroxyl groups of 50% or more is used have excellent emulsion stability.

Test Example B-2

A cocoa beverage was prepared by using the polyglycerol fatty acid ester obtained in each of Examples A-1 to A-8 or Comparative Examples A-1 to A-12 in accordance with the composition shown in Table B-3, and further subjected to fluidized bed granulation with a granulator using water as a binder. A 10 g portion thereof was gently added to 40 ml of water, and the mixture was allowed to stand for 4 hours. Thereafter, the liquid was gently removed by decantation, and the amount of the granular product sedimented at bottom without being dispersed in the liquid mixture was determined.

TABLE 5

Table B-3

| | Blending Amount (% by weight) |
|---|---|
| Cocoa Powder | 25 |
| Sugar | 60 |
| Lactose | 10 |
| Water | 4 |
| Polyglycerol Fatty Acid Ester | 1 |

TABLE 6

Table B-4

| | Polyglycerol | | | |
|---|---|---|---|---|
| | Hydroxyl Value | Primary Hydroxyl Groups (%) | Fatty Acid | Sedimented Amount |
| Ex. A-1 | 886 | 61.3 | Stearic Acid | ◉ |
| Ex. A-2 | 886 | 61.3 | Lauric Acid | ◉ |
| Ex. A-3 | 883 | 56.2 | Stearic Acid | ◉ |
| Ex. A-4 | 883 | 56.2 | Lauric Acid | ◉ |
| Ex. A-5 | 1148 | 52.5 | Stearic Acid | ○ |
| Ex. A-6 | 1148 | 52.5 | Lauric Acid | ○ |
| Ex. A-7 | 1148 | 52.5 | Myristic Acid | ○ |
| Ex. A-8 | 1148 | 52.5 | Oleic Acid | ○ |
| Comp. Ex. A-1 | 893 | 34.4 | Stearic Acid | X |
| Comp. Ex. A-2 | 893 | 34.4 | Lauric Acid | X |
| Comp. Ex. A-3 | 890 | 46.6 | Stearic Acid | Δ |
| Comp. Ex. A-4 | 890 | 46.6 | Lauric Acid | Δ |
| Comp. Ex. A-5 | 1165 | 32.2 | Stearic Acid | Δ |
| Comp. Ex. A-6 | 1165 | 32.2 | Lauric Acid | X |
| Comp. Ex. A-7 | 1165 | 32.2 | Myristic Acid | Δ |
| Comp. Ex. A-8 | 1165 | 32.2 | Oleic Acid | Δ |
| Comp. Ex. A-9 | 1160 | 38.5 | Stearic Acid | X |
| Comp. Ex. A-10 | 1160 | 38.5 | Lauric Acid | X |
| Comp. Ex. A-11 | 1350 | 53.5 | Stearic Acid | X |

TABLE 6-continued

Table B-4

| | Polyglycerol | | | |
|---|---|---|---|---|
| | Hydroxyl Value | Primary Hydroxyl Groups (%) | Fatty Acid | Sedimented Amount |
| Comp. Ex. A-12 | 1350 | 53.5 | Lauric Acid | Δ |

<Sedimented Amount>
◎: 0 g
○: 0.5 g or less
Δ: 0.5 to 1.0 g
X: 1.0 g or more
Here, ◎ and ○ are defined as acceptable products.

It is clear from Table B-4 that the powdered cocoa granules in which a polyglycerol having a hydroxyl value of 1200 or less and a ratio of primary hydroxyl groups of 50% or more is used have excellent dispersibility in water.

Test Example B-3

A cleansing cream was prepared by using the polyglycerol fatty acid ester obtained in each of Examples A-1 to A-8 or Comparative Examples A-1 to A-12 in accordance with the composition shown in Table B-5. As the preparation method, liquid paraffin was added dropwise to a mixture of each emulsifying agent, glycerol, 1,3-butylene glycol and purified water at 60° C. while mixing. The resulting composition was stored at 60° C. for 10 days.

TABLE 7

Table B-5

| | Blending Amount (% by weight) |
|---|---|
| Liquid Paraffin | 55 |
| Glycerol | 37 |
| 1,3-Butylene Glycol | 2 |
| Purified Water | 2 |
| Polyglycerol Fatty Acid Ester | 2 |

TABLE 8

Table B-6

| | Polyglycerol | | | |
|---|---|---|---|---|
| | Hydroxyl Value | Primary Hydroxyl Groups (%) | Fatty Acid | Stability |
| Ex. A-1 | 886 | 61.3 | Stearic Acid | ◎ |
| Ex. A-2 | 886 | 61.3 | Lauric Acid | ◎ |
| Ex. A-3 | 883 | 56.2 | Stearic Acid | ○ |
| Ex. A-4 | 883 | 56.2 | Lauric Acid | ○ |
| Ex. A-5 | 1148 | 52.5 | Stearic Acid | ◎ |
| Ex. A-6 | 1148 | 52.5 | Lauric Acid | ◎ |
| Ex. A-7 | 1148 | 52.5 | Myristic Acid | ○ |
| Ex. A-8 | 1148 | 52.5 | Oleic Acid | ◎ |
| Comp. Ex. A-1 | 893 | 34.4 | Stearic Acid | X |
| Comp. Ex. A-2 | 893 | 34.4 | Lauric Acid | Δ |
| Comp. Ex. A-3 | 890 | 46.6 | Stearic Acid | X |
| Comp. Ex. A-4 | 890 | 46.6 | Lauric Acid | Δ |
| Comp. Ex. A-5 | 1165 | 32.2 | Stearic Acid | X |
| Comp. Ex. A-6 | 1165 | 32.2 | Lauric Acid | Δ |
| Comp. Ex. A-7 | 1165 | 32.2 | Myristic Acid | X |
| Comp. Ex. A-8 | 1165 | 32.2 | Oleic Acid | Δ |
| Comp. Ex. A-9 | 1160 | 38.5 | Stearic Acid | Δ |
| Comp. Ex. A-10 | 1160 | 38.5 | Lauric Acid | X |
| Comp. Ex. A-11 | 1350 | 53.5 | Stearic Acid | X |
| Comp. Ex. A-12 | 1350 | 53.5 | Lauric Acid | Δ |

<Stability>
◎: no difference from that immediately after preparation
○: oil layer being separated (less than about 5% of oil component)
Δ: oil layer being separated (about 5% to 10% of oil component)
X: oil layer being separated (more than about 10% of oil component)
Here, ◎ and ○ are defined as acceptable products.

It is clear from Table B-6 that the cleansing creams in which a polyglycerol having a hydroxyl value of 1200 or less and a ratio of primary hydroxyl groups of 50% or more is used have excellent stability.

Test Example B-4

A solubilized preparation of MCT (medium-chain fatty acid monoglyceride) was prepared by using the polyglycerol fatty acid ester obtained in each of Examples A-1 to A-8 or Comparative Examples A-1 to A-12 in accordance with the composition shown in Table B-7. The polyglycerol fatty acid ester was warmed and melted, and the melted polyglycerol fatty acid ester was added to glycerol, and the mixture was warmed to 80° C. or more. The mixture was homogeneously mixed while stirring with a homomixer at 10,000 rpm, and MCT was gradually added thereto, and the mixture was stirred for 10 minutes. Thereafter, the mixture was cooled, and water was added thereto at an initial temperature of 60° C. and the mixture was homogeneously mixed, to finish the solubilized preparation. 0.1% Aqueous solutions of these preparations were prepared, and transparent solubility was confirmed.

TABLE 9

Table B-7

| | Blending Amount (% by weight) |
|---|---|
| Polyglycerol Fatty Acid Ester | 8.5 |
| Glycerol | 81 |
| MCT | 5.5 |
| Water | 5 |

TABLE 10

Table B-8

| | Polyglycerol | | | |
|---|---|---|---|---|
| | Hydroxyl Value | Primary Hydroxyl Groups (%) | Fatty Acid | Transparent Solubility |
| Ex. A-1 | 886 | 61.3 | Stearic Acid | ◉ |
| Ex. A-2 | 886 | 61.3 | Lauric Acid | ◉ |
| Ex. A-3 | 883 | 56.2 | Stearic Acid | ◉ |
| Ex. A-4 | 883 | 56.2 | Lauric Acid | ○ |
| Ex. A-5 | 1148 | 52.5 | Stearic Acid | ◉ |
| Ex. A-6 | 1148 | 52.5 | Lauric Acid | ◉ |
| Ex. A-7 | 1148 | 52.5 | Myristic Acid | ◉ |
| Ex. A-8 | 1148 | 52.5 | Oleic Acid | ○ |
| Comp. Ex. A-1 | 893 | 34.4 | Stearic Acid | Δ |
| Comp. Ex. A-2 | 893 | 34.4 | Lauric Acid | Δ |
| Comp. Ex. A-3 | 890 | 46.6 | Stearic Acid | Δ |
| Comp. Ex. A-4 | 890 | 46.6 | Lauric Acid | Δ |
| Comp. Ex. A-5 | 1165 | 32.2 | Stearic Acid | Δ |
| Comp. Ex. A-6 | 1165 | 32.2 | Lauric Acid | X |
| Comp. Ex. A-7 | 1165 | 32.2 | Myristic Acid | Δ |
| Comp. Ex. A-8 | 1165 | 32.2 | Oleic Acid | X |
| Comp. Ex. A-9 | 1160 | 38.5 | Stearic Acid | Δ |
| Comp. Ex. A-10 | 1160 | 38.5 | Lauric Acid | Δ |
| Comp. Ex. A-11 | 1350 | 53.5 | Stearic Acid | X |
| Comp. Ex. A-12 | 1350 | 53.5 | Lauric Acid | Δ |

<Transparent Solubility>
◉: transparent (transmittance: 98% or more)
○: slight white turbid being found (transmittance: 90% or more and less than 98%)
Δ: white turbid being found (transmittance: less than 90% of transmittance)
X: oil separation being found
Here, ◉ and ○ are defined as acceptable products.

It is clear from Table B-8 that the solubilized preparations in which a polyglycerol having a hydroxyl value of 1200 or less and a ratio of primary hydroxyl groups of 50% or more is used have excellent transparent solubility.

As demonstrated by the above Examples, according to the present invention, the polyglycerol fatty acid ester obtainable from a polyglycerol having a hydroxyl value of 1200 or less and a ratio of primary hydroxyl groups of 50% or more and a fatty acid as raw materials is capable of greatly reducing a surface tension of water, and the composition containing the polyglycerol fatty acid ester is capable of improving stability in quality. Therefore, it is obvious according to the present invention that the production of a perfectly solubilized product or a stable emulsion which has been so far impossible to be produced in the fields of foods, pharmaceuticals, and cosmetics is enabled.

INDUSTRIAL APPLICABILITY

The polyglycerol fatty acid ester of the present invention is effectively utilized in the fields of foods, pharmaceuticals, and cosmetics which necessitate solubilization, emulsification, or the like.

The invention claimed is:

1. A polyglycerol fatty acid ester formed by esterifying a polyglycerol and a fatty acid, wherein the polyglycerol has a hydroxyl value of 1200 or less and primary hydroxyl groups in an amount of 50% or more and 75% or less of the total hydroxyl groups.

2. An emulsified or solubilized composition comprising the polyglycerol fatty acid ester as defined in claim 1.

3. Foodstuff comprising the polyglycerol fatty acid ester as defined in claim 1.

4. Cosmetics comprising the polyglycerol fatty acid ester as defined in claim 1.

5. The polyglycerol fatty acid ester as defined in claim 1, wherein the primary hydroxyl group of the polyglycerol is 50% or more and 70% or less of the total hydroxyl groups.

6. An emulsified or solubilized composition comprising the polyglycerol fatty acid ester as defined in claim 5.

7. Foodstuff comprising the polyglycerol fatty acid ester as defined in claim 5.

8. Cosmetics comprising the polyglycerol fatty acid ester as defined in claim 5.

9. The polyglycerol fatty acid ester as defined in claim 1, wherein the primary hydroxyl group of the polyglycerol is 50% or more and 65% or less of the total hydroxyl groups.

10. An emulsified or solubilized composition comprising the polyglycerol fatty acid ester as defined in claim 9.

11. Foodstuff comprising the polyglycerol fatty acid ester as defined in claim 9.

12. Cosmetics comprising the polyglycerol fatty acid ester as defined in claim 9.

* * * * *